United States Patent
Schloderer et al.

(10) Patent No.: US 10,159,910 B2
(45) Date of Patent: Dec. 25, 2018

(54) SEALING MECHANISM AND SEALING METHOD

(71) Applicant: DIONEX SOFTRON GMBH, Germering (DE)

(72) Inventors: Richard Schloderer, Krailling (DE); Michael Wohner, Munich (DE)

(73) Assignee: DIONEX SOFTRON GMBH, Germering (DE)

( * ) Notice: Subject to any disclaimer, the term of this patent is extended or adjusted under 35 U.S.C. 154(b) by 991 days.

(21) Appl. No.: 14/484,740

(22) Filed: Sep. 12, 2014

(65) Prior Publication Data

US 2015/0069714 A1    Mar. 12, 2015

(30) Foreign Application Priority Data

Sep. 12, 2013  (DE) .......................... 10 2013 110 072

(51) Int. Cl.
G01N 1/00        (2006.01)
B01D 15/10       (2006.01)
F16J 15/02       (2006.01)
G01N 30/60       (2006.01)

(52) U.S. Cl.
CPC ............ B01D 15/10 (2013.01); *F16J 15/021* (2013.01); *F16J 15/028* (2013.01); *G01N 30/6026* (2013.01)

(58) Field of Classification Search
CPC ........ F16J 15/021; F16J 15/028; B01D 15/10; G01N 30/6026
See application file for complete search history.

(56) References Cited

U.S. PATENT DOCUMENTS

| | | | |
|---|---|---|---|
| 2,646,678 A | 7/1953 | Standing | |
| 3,361,261 A | 1/1968 | Fairey | |
| 4,470,910 A | 9/1984 | Quemerais et al. | |
| 5,104,131 A | 4/1992 | Edlund et al. | |
| 7,908,934 B2 | 3/2011 | Moshfegh et al. | |
| 2004/0100038 A1* | 5/2004 | Proper | F04B 53/164 277/500 |
| 2004/0256811 A1* | 12/2004 | Proper | F04B 53/164 277/500 |
| 2009/0028988 A1* | 1/2009 | Gunther | B29C 45/2806 425/564 |
| 2011/0037234 A1* | 2/2011 | Balsells | F16J 15/3212 277/562 |
| 2011/0247405 A1* | 10/2011 | Yasunaga | G01N 30/18 73/61.55 |
| 2012/0097026 A1* | 4/2012 | Almeida | F04B 53/04 92/5 R |

(Continued)

FOREIGN PATENT DOCUMENTS

| | | |
|---|---|---|
| CN | 101143270 A | 3/2008 |
| CN | 202700140 U | 1/2013 |

(Continued)

*Primary Examiner* — Gilbert Y Lee (57) ABSTRACT

The invention relates to a sealing mechanism and to a method which forms the basis for the former and in which a clamping ring which loads a sealing element compensates for an operationally induced change in the volume which is available for the sealing element, as a result of which the sealing action of the sealing element can be maintained reliably even in the case of high operating pressures.

22 Claims, 3 Drawing Sheets

(56) References Cited

U.S. PATENT DOCUMENTS

2013/0049302 A1\* 2/2013 Lemelin ............. G01N 30/6026
  277/345
2013/0323103 A1\* 12/2013 Shreve .................. F04B 1/0448
  417/437
2017/0074403 A1\* 3/2017 Almeida .............. F16J 15/3232

FOREIGN PATENT DOCUMENTS

| DE | 3828692 A1 | 3/1990 |
| DE | 202011100330 | 7/2011 |
| EP | 0148813 A2 | 8/1985 |
| JP | 2000035421 | 2/2000 |
| JP | 3315657 | 8/2002 |
| JP | 3315657 B2 | 8/2002 |

\* cited by examiner

SEALING MECHANISM AND SEALING METHOD

CROSS REFERENCE TO RELATED APPLICATIONS

This application claims the priority benefit under 35 U.S.C. § 119 to German Patent Application No. 10 2013 110 072.4, by Richard SCHLODERER and Michael WOHNER for "Sealing Mechanism and Sealing Method" filed on Sep. 12, 2013, the disclosure of which is incorporated herein by reference.

FIELD OF THE INVENTION

The invention relates to a sealing mechanism and to a sealing method for sealing an interior space which can be loaded with high internal pressure.

BACKGROUND

In particular in the case of HPLC (high performance liquid chromatography) processes, in which operation is carried out at very high pressures, high requirements are made of the seals. Belonging to processes of this type are, for example, pumps, in which pressures of over 100 MPa occur. Although attempts have been made in the prior art to assist a satisfactory sealing action by way of a manufacturing tolerance which is as narrow as possible, the high pressures which occur have up to now not permitted any satisfactory solutions. Embodiments are known, in which annular sealing elements are prestressed in the axial direction, in order to achieve a desired sealing action. The increased internal pressure which occurs during operation leads, however, to the components which are sealed with respect to one another being pressed apart, with the result that the prestressing pressure which is introduced into the seal and therefore the sealing action also decrease. Correspondingly, the prestressing pressure previously has to be set to be sufficiently high above the operating pressure to be expected.

Elements for cleaning or mixing liquids are frequently also used within high pressure systems of this type. They have to be exchangeable, with the result that a satisfactory sealing action of the components which receive them and can be released from one another is required. At the same time, the filter or mixer within the system also has to be sealed in such a way that no medium can flow past it, but rather exclusively through it. Here, the filters or mixers which are used in HPLC technology frequently have manufacturing tolerances which are to be taken into consideration in the sealing action. For instance, sintered metallic frits are known which have a specific porosity and pore width. They can be disk-shaped with a diameter up to the centimeter range and a thickness of a few millimeters.

DE 38 38 692 A1 has disclosed an arrangement for sealing a rod which is moved to and fro, in which arrangement a sealing ring is seated in a groove and circumferentially loads the rod with one edge for sealing purposes. A deformable clamping ring loads the sealing ring in the radial direction. It was therefore an object of the invention to provide a method for sealing and a device for carrying out the method, in order for it to be possible to achieve a reliable sealing action in a simple way even at very high operating pressures.

SUMMARY

The invention is based on the finding that the prestress which is introduced into a sealing element should as far as possible be maintained even when the internal pressure increases, in order for it to be possible to ensure the sealing action in an unchanged state. According to the invention, this takes place by way of the use of a clamping ring which adjoins the sealing element radially and widens or contracts radially depending on the internal pressure. As a result, the sealing element which is arranged radially with respect to the clamping ring experiences pressure loading by way of the clamping ring, which pressure loading is dependent on the internal pressure and compensates for a decrease in the prestressing force on account of increased internal pressure. The sealing action of the sealing element can therefore be maintained even in the case of rising internal pressure.

The method according to the invention serves to seal an interior space which can be loaded with high internal pressure, the interior space being formed substantially by a housing and a pressing part which can be connected to the housing and extending in an approximately rotationally symmetrical manner about an imaginary axis Z. In particular, it can be a chamber in an HPLC component which can be provided, for example, for receiving a disk-shaped frit. The pressing part can be connected to the housing (in particular by way of a screw mechanism), as a result of which the interior space is formed between the pressing part and the housing. A preferably annular sealing element can be inserted concentrically with respect to the Z-axis into a seat on the housing or on the pressing part, which sealing element is loaded with a prestress during connection or screwing of the housing to the pressing part. According to the invention, the prestress is selected to be so high that the sealing element is deformed in the process.

The clamping ring according to the invention is preferably provided radially on the inside and concentrically with respect to the sealing element and so as to bear tightly against the latter, which clamping ring has a certain elasticity in the radial direction and can be formed, for example, from a titanium-containing material. The sealing element is enclosed as tightly and completely as possible by the housing, the pressing part and the clamping ring. During the pressing of the pressing part into the housing, the sealing element is loaded in the axial direction with a prestress which leads to the deformation of the sealing element in the radial direction. As a result, the clamping ring is loaded on its outer side to such a pronounced extent that it is compressed by an amount in the radial direction toward the Z-axis and in the process receives a clamping force which results from its deformation. After this mounting, in which ambient pressure preferably still prevails in the interior space, the sealing element is then prestressed between the housing, the pressing part and the clamping ring to such a pronounced extent that a pressure prevails in its interior, which pressure lies substantially above the operating pressure to be expected in the interior space and radially compresses the clamping ring which adjoins the sealing element radially on the inside in accordance with its elasticity properties.

If the interior space is subsequently loaded with the operating pressure, this drives the housing and the pressing part apart from one another in the axial direction by an amount, depending on the material properties and manufacturing tolerances. In the seals which are known from the prior art and predominantly act in the axial direction, this leads to leakiness if the conventional sealing element is not capable on its own of compensating for this axial movement. In contrast, the clamping ring according to the invention which is loaded on the inner side by the introduced operating pressure and is widened radially again by an amount as a result then exerts additional pressure on the sealing element which adjoins its circumference radially, is deformed in the radial direction so as to follow this pressure, adapts as far as possible to the changed seat cross section in the process and maintains its sealing action in an unchanged manner.

The sealing action is produced particularly satisfactorily when the sealing element, during its loading in the seat with the prestressing force, is loaded to such a pronounced extent that it flows plastically. For a sealing ring which is configured, for example, from PEEK, a pressure of greater than 300 MPa would be expedient. As a result of the plastic flow, the sealing ring, the seat of which between the housing, the pressing part and the clamping ring is delimited by narrow tolerances and very small gaps, can fill said gaps satisfactorily and seal them reliably. The sealing element maintains these plastic properties even and precisely when the interior space is loaded with operating pressure, with the result that its sealing properties which result from the deformability are maintained at all times.

According to a further advantageous embodiment of the invention, a disk-shaped frit which is arranged within the clamping ring is clamped in via the clamping ring which is deformed radially to the inside by way of the loaded sealing element. It can preferably be plastically deformed permanently (reduced in diameter) and at any rate can be held by the clamping ring in such a way that a leakage flow between the frit and the clamping ring is ruled out reliably. Here, the radial widening of the clamping ring which occurs when the internal pressure is increased is too small for the frit within the clamping ring to be capable of being released in the process.

The permitted deformation of the frit during the mounting of the sealing mechanism produces a further advantage which facilitates the mounting per se. The manufacturing-induced tolerances of the sealing ring, the clamping ring and the resulting sealing gaps entail the requirement of achieving the prestressing forces which are provided for the mounting in a manner which is reliable, reproducible and independent of tolerances. To this end, the clamping ring which is inserted in the housing is used as a stop for the pressing part which is therefore always pressed into the housing during mounting to such an extent until it bears against the clamping ring in the axial direction. At the same time, the sealing element which is arranged radially outside the clamping ring is also loaded by the pressing part by way of the push-in movement of the pressing part, optionally by way of a projection on the pressing part, which projection protrudes specifically into the seat. Here, the geometry of the clamping ring, the sealing element and the housing and the pressing part is selected in such a way that, at the point at which the pressing part comes into contact with the clamping ring during pushing in or screwing in, the sealing element is already loaded with such a high prestressing force that it loads the clamping ring such that it is deformed in the radial direction to the inside.

Here, a frit which is held within the clamping ring and can have external diameters which vary on account of manufacturing tolerances is loaded with pressure in the radial direction to such an extent that it is adapted to the internal diameter of the clamping ring by way of plastic deformation. The frit can follow radial widening of the clamping ring which is to be expected later under operating pressure by way of purely elastic deformation and therefore remains firmly clamped into the clamping ring in all operating states.

On account of the plastic deformability of the frit, tolerance compensation during first-time screwing together of the arrangement is achieved in this way. Here, the frit is deformed plastically to such an extent that the pressing part always lies on the clamping ring independently of the tolerances, which clamping ring is supported for its part on the housing. Unlike in the prior art, in which the prestressing force which is to be introduced into a sealing element frequently has to be set according to feeling, the clamping ring provides a simple mounting aid as a defined stop for the pressing part, by way of which mounting aid a frit which is subject to tolerances is held reliably in every case in the prestressed clamping ring which, as a result of operationally induced widening, at the same time can load the sealing element for continuous reliable sealing.

The above-described principle of sealing with the aid of a radially operating clamping ring can be used for a very wide variety of sealing tasks. In particular for HPLC technology, in which very high pressures occur, this principle is superior to the conventional sealing processes which are known from the prior art with predominantly axially acting sealing elements. It is to be noted here that, although the arrangement of the sealing element radially outside the clamping ring represents one preferred embodiment, it is not necessary for implementing the inventive basic concept. Instead, it would also be conceivable in principle to arrange the clamping ring which is deformed radially by way of the sealing element outside the sealing element, that is to say such that it runs around the latter. This is readily possible, for example, when frits are to be used as rigid plates, for example made from ceramic.

In this variant, the clamping ring acts as an element which runs around the sealing element and loads it radially to the inside. The sealing element which is loaded axially first of all during mounting then exerts a radial clamping force both to the inside on the immediately adjoining frit and to the outside on the clamping ring. This leads to firm clamping of the frit within the sealing element and to widening of the clamping ring. Here, the cross section of the sealing element changes slightly, said sealing element filling the volume which is opened by way of the widening of the clamping ring. Here, the sealing gaps are correspondingly to be dimensioned in such a way that a passage of the plastically flowing sealing element is possible only in regions which are provided for this purpose. At a subsequently increased internal pressure, at which the pressing part rises up slightly from the housing in the axial direction, the sealing element assumes the volume of the gap which is produced in the process. Here, with a reduction in its diameter, the clamping ring supplies a counterforce from the outside against the sealing element which is adapted in a plastically flowing manner to the newly produced shape of its seat and therefore maintains its sealing function even when the pressing part rises up slightly from the housing in the axial direction.

BRIEF DESCRIPTION OF THE DRAWINGS

One advantageous embodiment of the invention is to be explained in greater detail in the following text using one example from the Figures.

DETAILED DESCRIPTION OF EMBODIMENTS

Figure 1:
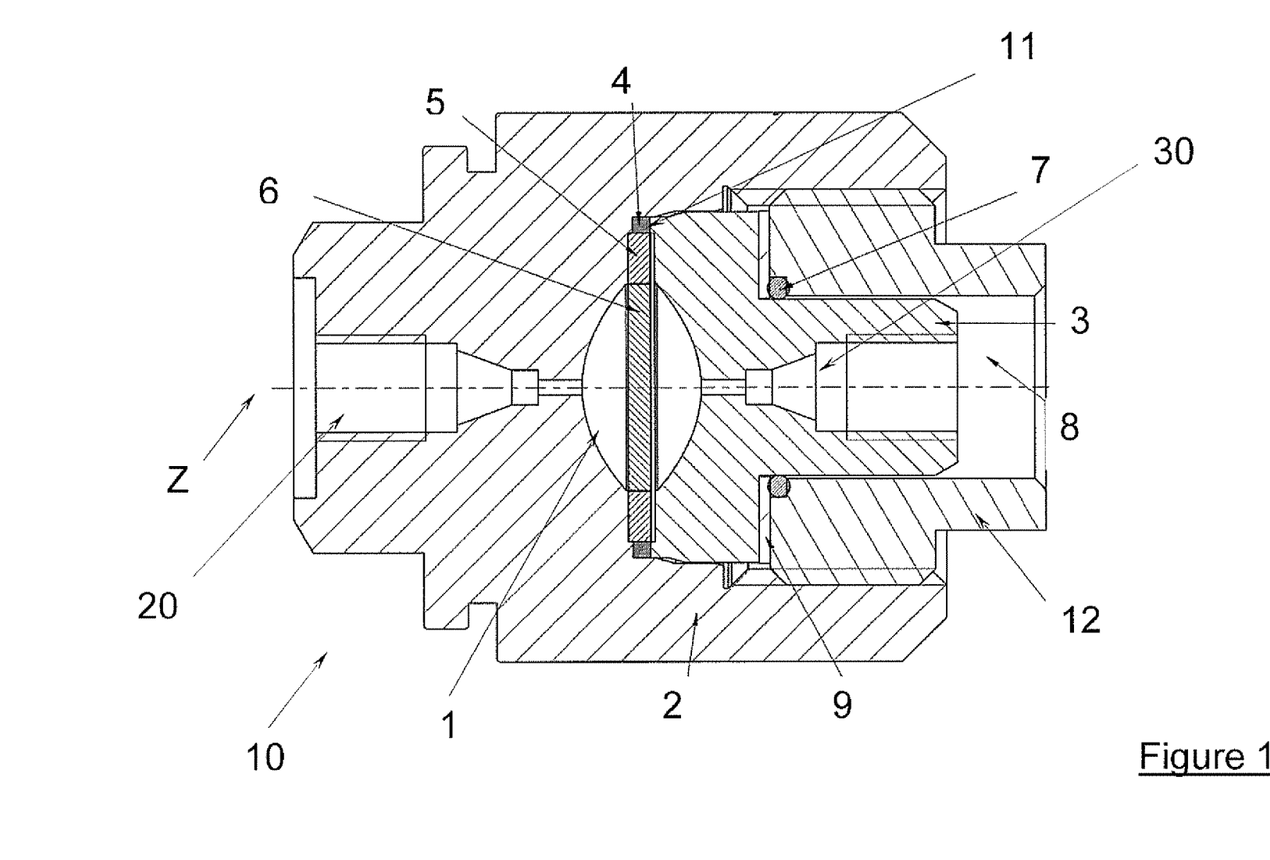
FIG. 1 shows a diagrammatic sectional illustration of a sealing mechanism according to the invention.

FIG. 1 shows a connecting part from HPLC technology, which connecting part makes it possible to receive an exchangeable frit 6 and which is designed for operating pressures of more than 100 MPa. The sealing mechanism 10 which is shown comprises a housing 2 which is of substantially rotationally symmetrical configuration about an axis Z. A pressing part 3 can be pushed through an open end of the housing 2 into the latter along the Z-axis. A screw-in piece 12 which loads the pressing part 3 on the rear side can be screwed for this purpose into the housing 2 in the Z-direction along a thread, as a result of which the pressing part 3 can be pushed or can be firmly clamped into the housing 2 (from the right to the left in FIG. 1). The housing 2 and the pressing part 3 have connector channels 20 and 30, respectively, through which medium can be introduced into and discharged from an interior space 1 which is formed by the housing 2 and the pressing part 3 under high pressure. Here, the medium is to be guided through the disk-shaped frit 6 which is arranged in the interior space 1 concentrically with respect to the Z-axis. The maximum diameter of the interior space 1 coincides approximately with the external diameter of the frit 6. Leakage flows which lead around the frit 6 are to be avoided.

A clamping ring 5 made from a titanium compound runs around the frit 6 and bears with an end side against the housing 2. The pressing part 3 can be pushed into the housing 2 until it comes into contact with the other end side of the clamping ring 5 which, as a result, defines the end position of the pressing part 3 relative to the housing 2 (in FIG. 1, a small gap which is still to be explained is indicated instead between the pressing part 3 and the clamping ring 5).

A sealing element 4 made from a PEEK material is once again arranged radially outside the clamping ring 5. A step-shaped shoulder within the housing and the outer face of the clamping ring 5 form a seat for the sealing element 4. An axial projection 11 which is of annular configuration on the pressing part 3 acts on the sealing element 4 even before the pressing part 3 comes into contact with the clamping ring 5. The sealing element 4 is enclosed as completely as possible in its seat by the housing 2, the clamping ring 5 and the pressing part 3 with narrow gaps between said individual components.

Figure 2:
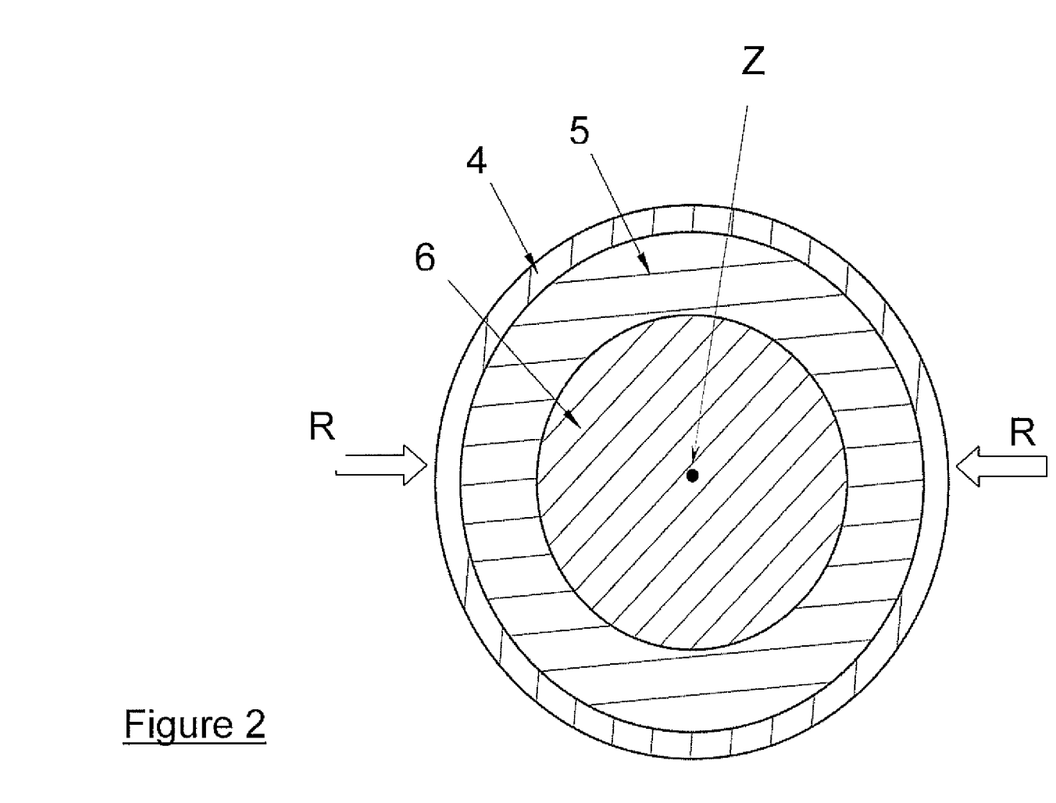
FIG. 2 shows a simplified sectional view of a frit with a clamping ring and a sealing element.

FIG. 2 shows a section through the frit 6 with a circumferential clamping ring 5 which in turn is enclosed by the sealing element 4.

The sealing mechanism 10 functions as follows: when the screw-in piece 12 and the pressing part 3 are removed, the frit 6 which can be inserted in a hand-tight manner into the clamping ring 5 here is inserted into the housing 2. The sealing element 4 is also inserted into its seat. The pressing part 3 is subsequently moved by means of the screw-in piece 12 in the axial direction toward the arrangement comprising frit 6, clamping ring 5 and sealing element 4. An O-ring 7 or a sliding disk 9 between the screw-in piece 12 and the pressing part 3 facilitates this. The O-ring 7 and the sliding disk 9 are optional here. The sliding disk serves to minimize the friction between the screw-in piece 12 and the pressing part 3 and thus to keep the required torque low. The O-ring 7 in turn serves to protect the sliding disk 9, for example made from brass, against liquid which penetrates (corrosion).

During the further advance of the pressing part 3 (from the right to the left in FIG. 1), the annular projection 11 comes into contact with the sealing element 4 and loads it with a prestressing force. The geometry of all the components which enclose the sealing element 4 in the process is selected in such a way that the sealing element 4 can be loaded by way of the projection 11 until it begins to flow plastically, even before the pressing part 3 finally comes into contact with the clamping ring 5 and, as a result, the pushing-in movement of the pressing part 3 is ended. As a result of the high prestressing force which is introduced into the sealing element 4 in the process and acts in the radial direction R to the inside on the clamping ring 5, its diameter is reduced elastically with the absorbing of a clamping force. At the same time, the plastically flowing sealing element 4 reliably seals the narrow gaps which exist between the pressing part, the housing and the clamping ring.

The deformation of the clamping ring 5 radially to the inside acts on the frit 6 which is held in the interior of the clamping ring 5, is adapted by way of plastic deformation to the narrower internal diameter of the clamping ring 5 and, as a result, is held very firmly by the latter. A leakage flow between the frit and the clamping ring can be avoided as a result.

After this mounting, the sealing mechanism is ready for use, in which the interior space 1 is loaded with high pressure by way of medium which flows in. This internal pressure leads to the pressing part 3 being pressed away from the housing 2 by a small amount (from the left to the right in FIG. 1), as a result of which a small gap also occurs between the pressing part 3 and that end face of the clamping ring 5 which faces it (this state is shown in FIG. 1). With the increasing internal pressure, the clamping ring 5 is also additionally loaded in the radial direction, as a result of which it is widened again in the radial direction by an amount. As a result, the sealing element 4 experiences radial loading which acts from the inside to the outside. Although the annular projection 11 moves away somewhat from the sealing element 4 in the axial direction during the pressure loading, with the result that a gap might also be produced there, since the clamping ring 5 displaces the volume of the plastically flowing sealing element 4 in the radial direction during its expansion, the sealing element 4 is adapted directly to its slightly changed seat, as a result of which constantly satisfactory sealing of the gaps around the sealing element is ensured. In this way, the effect according to the invention is brought about, namely that the pressure in the material of the sealing element 4 is maintained by way of the elastic clamping ring 5 even when the housing 2 and the pressing part 3 perform small relative movements with respect to one another and the volume which is available for the sealing element is increased.

Figure 3:
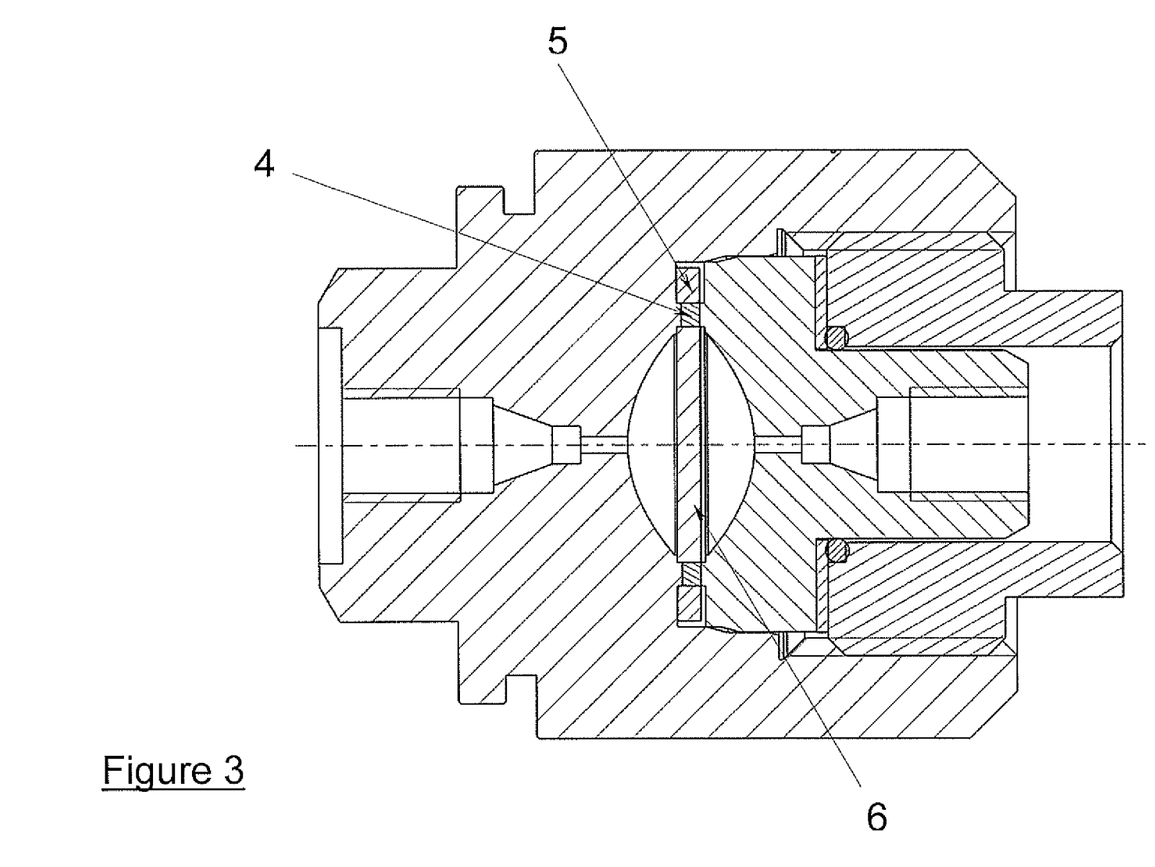
FIG. 3 shows a sealing mechanism with a clamping ring which runs around the sealing element.

FIG. 3 shows a sealing mechanism which is largely consistent with that from FIG. 1, with the result that the repetition of almost all designations can be dispensed with. In this embodiment, the arrangement of the sealing element 4 and the clamping ring 5 is swapped in the radial direction. The clamping ring 5 runs around the sealing element 4 which for its part encloses a centrically arranged frit 6. In the unscrewed state, the ring is held in position by way of the geometry of its seat in the housing.

During mounting, the screw-in piece 12 exerts an axial force on the pressing part 3. Here, the sealing element 4, for example made from PEEK, is loaded in such a way that it is deformed and begins to flow. The clamping ring 5 which lies around the sealing element 4 absorbs the force which occurs in the radial direction. A gap toward the housing is provided radially outside the clamping ring 5, in order to make an expansion of the clamping ring 5 possible. To the inside, the sealing element 4 can bear directly against the frit or disk 6, for example made from ceramic. Here, the frit 6 has to be sufficiently rigid to absorb the pressure which occurs of the prestressed sealing element 4.

Under operating pressure, the sealing element 4 can fill the gaps which result on account of the increased pressure between the housing 2 and the pressing part 3. Here, the clamping ring 5 which is resilient to the inside acts on the sealing element 4 radially from the outside and can compensate for volumetric changes of the sealing element 4 in the axial direction by way of a reduction in the radial direction.

What is claimed is:

1. A method for sealing an interior space of a device, the device configured to be loaded with a high internal pressure in the interior space, the interior space being formed substantially by a housing and a pressing part, the pressing part being connected to the housing, the device comprising a sealing element configured to be about a central axis of the device and clamped in between the pressing part and the housing, the method comprising:
   a) pushing of the pressing part into the housing to form the interior space and load the sealing element with a selectable prestress, in which the pressing part is pressed into a seat and deforms the sealing element;
   b) loading of a clamping ring which adjoins the sealing element radially with the deformed sealing element to introduce a radial clamping force for deforming the clamping ring.

2. The method as claimed in claim 1, wherein the loading of the sealing element takes place in a direction along the central axis in the method step a).

3. The method as claimed in claim 1, wherein the clamping ring is at least partially reversibly deformed by way of the loading with the sealing element.

4. The method as claimed in claim 1, wherein the deforming of the clamping ring is reversed at least partially by way of an increase in an internal pressure of the internal space.

5. The method as claimed claim 1, in which the clamping ring is elastically deformed when exposed to variations of an internal pressure of the internal space to keep the prestress in the sealing element largely constant or a plastic flow of the sealing element maintains a sealing action.

6. The method as claimed in claim 1, wherein a frit is in an interior of the clamping ring for filtering or mixing a medium guided through the interior space.

7. The method as claimed in claim 6, wherein the sealing element is pressed into a seat on the housing or the pressing part, wherein the frit is clamped in an interior of the clamping ring, directly or via the sealing element in between the frit and the clamping ring.

8. The method as claimed in claim 7, wherein the frit is at least partially irreversible deformed plastically.

9. The method as claimed in claim 1, wherein the clamping ring is arranged between the pressing part and the housing, the clamping ring is used on both sides in an axial direction along the central axis as a stop for the pressing part or the housing when the sealing element is pressed into a seat on the housing or the pressing part.

10. The method as claimed in claim 1, wherein the interior space is part of an HPLC system.

11. The method of claim 1, wherein the radial clamping force deforms the clamping ring inwardly.

12. The method of claim 1, wherein the high internal pressure is greater than 100 MPa.

13. The method of claim 1, wherein the high internal pressure is over 100 MPa.

14. A sealing mechanism for a HPLC component, the sealing mechanism comprising:
   an interior space configured to be loaded with a high internal pressure and is formed substantially by a housing and a pressing part, the pressing part configured to be connected to the housing,
   a sealing element configured to be pressed into a seat between the pressing part and the housing and the sealing element extends about a central axis of the sealing mechanism,
   wherein an elastic clamping ring is formed about the central axis and configured to be deformed radially by the sealing element or on the internal pressure provided between the pressing part and the housing as the pressing part is pressed into the housing.

15. The sealing mechanism of claim 14, further comprising a frit dividing the interior space into two regions, the frit being arranged within the clamping ring or within the sealing element, the sealing mechanism being configured to allow a medium to enter into a first region to pass through the frit to a second region.

16. The sealing mechanism of claim 14, wherein the sealing element is a ring around an outer side of the clamping ring, the clamping ring configured to hold a frit arranged in the clamping ring under radial prestress.

17. The sealing mechanism of claim 14, wherein the pressing part is configured to be connected to the housing so that the sealing element is pressure-loaded in a direction along the central axis to cause plastic flow of the sealing element and exert a clamping force on the clamping ring in a radial direction by way of the sealing element.

18. The sealing mechanism of claim 14, wherein the clamping ring forms an axial stop for the pressing part during the connection of the pressing part to the housing.

19. The sealing mechanism of claim 14, wherein the housing forms a seat for the sealing element, the sealing element being annular with respect to the central axis and the housing surrounds an outer side of the sealing element, the sealing element bearing on an inner side against the clamping ring, the clamping ring being formed about the central axis and around a frit, and a section of the pressing part deforming the sealing element during the connection to the housing, and a further section of the pressing part moved against the clamping ring.

20. The sealing mechanism of claim 19, wherein the section of the pressing part includes an axial projection of an annular configuration where the axial projection contacts the sealing element.

21. The sealing mechanism of claim 14, wherein the housing is configured to be rotationally symmetrical along the central axis.

22. A method of using a sealing mechanism for a HPLC component, the sealing mechanism including an interior space configured to be loaded with a high internal pressure and is formed substantially by a housing and a pressing part, the pressing part configured to be connected to the housing, a sealing element configured to be pressed into a seat between the pressing part and the housing and the sealing element extends about a central axis of the sealing mechanism, wherein an elastic clamping ring is formed about the central axis and configured to be deformed radially by the sealing element or on the internal pressure provided between the pressing part and the housing as the pressing part is pressed into the housing, the method comprising:
   loading the interior space with the high internal pressure, the high internal pressure being greater than 100 MPa;
   pressing with the high internal pressure the pressing part away from the housing to form a gap in between the pressing part and an end face of the clamping ring;
   widening the clamping ring in a radial direction; and radially loading the sealing ring from the widened clamping ring, whereby the sealing action is maintained.

* * * * *

UNITED STATES PATENT AND TRADEMARK OFFICE
CERTIFICATE OF CORRECTION

PATENT NO. : 10,159,910 B2
APPLICATION NO. : 14/484740
DATED : December 25, 2018
INVENTOR(S) : Schloderer et al.

Page 1 of 1

It is certified that error appears in the above-identified patent and that said Letters Patent is hereby corrected as shown below:

Column 7, Line 33, Claim 5 should read:
5. The method as claimed in claim 1, in which the clamping Signed and Sealed this
Twenty-third Day of July, 2019

Andrei Iancu
*Director of the United States Patent and Trademark Office*